(12) United States Patent
Shakerian et al.

(10) Patent No.: US 10,481,114 B1
(45) Date of Patent: Nov. 19, 2019

(54) PROBE AND SAMPLE HOLDER FOR MAGNETIC RESONANCE AND MAGNETIC RESONANCE IMAGING

(71) Applicant: University of New Brunswick, Fredericton (CA)

(72) Inventors: Mojtaba Shakerian, Fredericton (CA); Bruce J. Balcom, Fredericton (CA)

(73) Assignee: University of New Brunswick, Fredericton, NB (CA)

( * ) Notice: Subject to any disclaimer, the term of this patent is extended or adjusted under 35 U.S.C. 154(b) by 50 days.

(21) Appl. No.: 15/675,343

(22) Filed: Aug. 11, 2017

(51) Int. Cl.
G01N 24/08 (2006.01)
G01R 33/30 (2006.01)
G01R 33/54 (2006.01)
G01R 33/48 (2006.01)

(52) U.S. Cl.
CPC ........... *G01N 24/08* (2013.01); *G01R 33/305* (2013.01); *G01R 33/307* (2013.01); *G01R 33/4818* (2013.01); *G01R 33/54* (2013.01)

(58) Field of Classification Search
CPC ............ G01R 33/5676; G01R 33/5673; G01R 33/567; G01R 33/5659; G01R 33/56581; G01R 33/56572; G01R 33/56563; G01R 33/56554; G01R 33/56545; G01R 33/56536; G01R 33/56527; G01R 33/56518; G01R 33/56509; G01R 33/565; G01R 33/56391; G01R 33/56383; G01R 33/56375; G01R 33/56366; G01R 33/56358; G01R 33/5635; G01R 33/56341; G01R 33/56333; G01R 33/56325; G01R 33/56316; G01R 33/56308; G01R 33/563
See application file for complete search history.

(56) References Cited

U.S. PATENT DOCUMENTS

| | | | |
|---|---|---|---|
| 5,433,717 A * | 7/1995 | Rubinsky | A61B 18/02 600/411 |
| 2014/0194728 A1 * | 7/2014 | Vahala | A61N 7/02 600/411 |
| 2014/0253116 A1 | 9/2014 | Freedman et al. | |

OTHER PUBLICATIONS

C. E. Muir and B. J. Balcom, Annual reports on NMR Spectroscopy (Academic Press, Burlington, 2012) edited by G. A. Webb, p. 81-113.
(Continued)

*Primary Examiner* — Tung X Nguyen
(74) *Attorney, Agent, or Firm* — Eugene F. Derényi; Fogler, Rubinoff LLP (57) ABSTRACT

A core holder for a reservoir rock core sample for MR or MRI measurement including a casing and a chamber internal to the core holder, an inlet and an outlet in the core holder for circulating a confining fluid in the chamber, a sample housing in the chamber for containing the core sample, the sample housing including an inlet and an outlet in the sample holder for circulating fluid to and from the sample, and a membrane for isolating the sample from fluid contact with the confining fluid but permitting fluid pressure to be exerted on the sample when the confining fluid is pressurized, the space in the chamber not occupied by the sample housing defining a void space, an RF probe in the void space and at least partially surrounding the sample housing, whereby confining fluid introduced into the chamber circulates in the void space around the RF probe.

12 Claims, 6 Drawing Sheets

(56) References Cited

OTHER PUBLICATIONS

G. R. Coates, L. Xiao, and Manfred G. Prammer, NMR Logging Principles & Applications (Halliburton Energy Services, Houston, 1999), pp. 33-76.

D. Tiab and E.C. Donaldson, Petrophysics theory and practice of measuring reservior rock and fluid trasnport propertties 2th edition (Gulf professionmal publishing, Burlington, 2004), pp. 29-86.

Delivering success in HP/HT reserviors through experience, innovation and reliable technologies (Halliburton, Houston, 2011).

Y. Zhao, Y. Song, Y. Liu, H. Liang, and B. Dou, Visualization and Measurement of CO2 Flooding in Porous Media Using MRI, Ind. Eng. Chem. Res. 50, 4707 (2011).

Y. Song, N. Zhu, Y. Zhao, Y. Liu, L. Jiang, and T. Wang, Magnetic resonance imaging study on near miscible supercritical CO2 flooding in porous media, Phys. Fluids. 25, 053301 (2013).

H. Liu, M. Hunter, S. Obruchkov, E. Mccarney, M. Robinson, R. Dykstra, and P. Galvosas, Characterizing fluid presence and transport in rock cores at reservoir-like conditions via spatially resolved NMR relaxation/diffusion maps: The proceedings of the 31st International Symposium of the Society of Core Analysts, 'St. John's, Canada, Aug. 16-21, 2015, pp. 143-155.

G. Ersland, J. Husebo, A. Graue, B. A. Baldwin, J. Howard, and J. Stevens, Measuring gas hydrate formation and exchange with CO2 in Bentheim sandstone using MRI tomography, Chem. Eng. J. 158, 25 (2010).

S. A. Bagherzadeh, I. L. Moudrakovski, J. A. Ripmeester, and P. Englezos, Magnetic Resonance Imaging of Gas Hydrate Formation in a Bed of Silica Sand Particles, Energy. Fuels. 25, 3083 (2011).

H. Han, M. M Ouellette, B. Mavmillan, F. Goora, R. Macgregor, D. Green, and B.J. Balcom, High pressure magnetic resonance imaging with metallic vessels, J. Magn. Reson. 213, 90 (2011).

M. Ouellette, M. Li, G. Liao, E.M.A. Hussein, L. Romero-Zeron, and B.J. Balcom, Rock Core Analysis: Metallic Core Holders for Magnetic Resonance Imaging Under Reservoir Conditions, In Mobile NMR and MRI: Developments and Applications, edited by M.L. Johns, E.O. Fridjonsson, S. J. Vogt, and A. Haber (Royal Society of Chemistry, Cambridge, 2016), p. 290-309.

A. Afrough, M. Shakerian, S. Zamiri, B. Macmillan, F. Marica, B. Newling, L. Romero-Zeron, and B.J. Balcom, Magnetic-Resonance Imaging of High-Pressure Carbon Dioxide Displacement: Fluid/Surface Interaction and Fluid Behavior, SPE Journal (2018), 1-16.

L. L. Latour, R. L. Kleinberg, A. Sezginer, Nuclear Magnetic Resonance Properties of Rocks at Elevated Temperatures, J. Colloid. Interface. Sci. 150, 535 (1992).

R. Morrison, Grounding and shielding: circuits and interference, Wiley—IEEE Press, 2007, pp. 18.

R. Freedman, V. Anand, B. Grant, K. Ganesan, P. Tabrizi, R. Torres, D. Catina, D. Ryan, C. Borman, and C. Krueckl, A compact high-performance low-field NMR apparatus for measurements on fluids at very high pressures and temperatures, Rev. Sci. Instrum. 85, 025102 (2014).

D. I. Hoult, The Principle of Reciprocity in Signal Strength Calculations} A Mathematical Guide, Concepts Magn. Reson. 12, 173 (2000).

R. Solechi and R.J. Conant, Advanced Mechanics of Materials (Oxford University Press, Inc., New York, 2003), pp. 95-160.

M. A. Andersen, B. Duncan, J. A. Ripmeester, and R. Mclin, Core Truth in Formation Evaluation, Oilfield Review. 25(2),16-25 (2013).

J. C. Seferis, Polyetheretherketone (PEEK): Processing-Structure and Properties Studies for a Matrix in High Performance Composites, J. Compos. Mater. 3(4), 158 (1986).

M. Mehdizadeh, Microwave/RF Applicators and Probes for Material Heating, Sensing, and Plasma Generation A Design Guide (William Andrew, Oxford, 2010), pp. 2-34.

A. G. Webb, Dielectric Materials in Magnetic Resonance, Concepts Magn. Reson. 38A (4), 148 (2000).

J. Mispelter, NMR Probeheads for Biophysical and Biomedical Experiments: Theoretical Principles and Practical Guidelines (Imperial College press, London, 2006), pp. 1-91.

W. T. Mclyman, Transformer and inductor design handbook 3th edition, revised and expanded, (Marcel Dekker, Inc, New York, 2004), pp. 456-458.

J Mitchell, J. Staniland, and R. Chassanne, E. J. Fordham, Quantitative In Situ Enhanced Oil Recovery Monitoring Using Nuclear Magnetic Resonance, Transp. Porous. Med. 94, 683 (2012).

C. H. Collie, J. B. Hasted and D. M. Ritson, The Dielectric Properties of Water and Heavy Water, Proc. Phys. Soc. 60 (2), 145 (1947).

C. H. Wu, C. V. Grant, G. A. Cook, S. H. Park, S. J. Opella, A strip-shield improves the efficiency of a solenoid coil in probes for high-field solid-state NMR of lossy biological samples, J. Magn. Reson. 200, 74 (2009).

S. W. Atlas, Magnetic resonance imaging of the brain and spine 4th edition, (Lippincott williams & wilkins, PA, 2009), pp. 13-18.

D. P. Dewitt, Fundamentals of Heat and Mass Transfer, (John Wiley & Sons, Inc., New York, 1996), pp. 581-619.

A. Valori, J. Mitchell, and E. J. Fordham, Digital filters for low-field NMR, Concepts. Magn. Reson. 46(B), 202 (2016).

R. K. Minard, A. R. Wind, Solenoidal Microcoil Design. Part I: Optimizing RF Homogeneity and Coil Dimensions, Concepts. Magn. Reson. 13(2), 128 (2001).

S Vashaee, B. Newling, B. Macmillan and B. J. Balcom, B1 mapping with a pure phase encode approach: Quantitative density profiling, J.Magn. Reson. 232, 68 (2013).

P. J. Prado, B. J. Balcom, I. V. Mastikhin, A. R. Cross, R. L. Armstrong, and A. Logan, Single-Point Magnetic Resonance Imaging Study of Water Adsorption in Pellets of Zeolite 4A, J.Magn. Reson. 137, 324 (1999).

G. J. Hirasaki, S. W. Lo, Y. Zhang, Y, NMR properties of petroleum reservoir fluids, Magn. Reson. Imaging. 21, 269 (2003).

* cited by examiner

PROBE AND SAMPLE HOLDER FOR MAGNETIC RESONANCE AND MAGNETIC RESONANCE IMAGING

BACKGROUND OF THE INVENTION

Field of the Invention

The present invention relates generally to probe and sample holders for magnetic resonance and magnetic resonance imaging.

Background

Magnetic resonance imaging (MRI) and magnetic resonance (MR) are non-invasive techniques commonly employed to study the microscopic and macroscopic properties of fluids in samples such as petroleum reservoir core plugs[1,2]. Well-developed MR/MRI methods can determine the wettability and other fluid/core plug properties[1,2]. MR/MRI can characterize oil, gas and water fractions in the fluid mixture saturating core plugs[1,2]. Fluid properties of course vary with pressure and temperature[3]. Pressure and temperature of petroleum reservoirs can change from atmospheric pressure at 20° C. in shallow gas reservoirs to 20000 psi at 200° C. in deepwater wells[3,4]. Core plug MR/MRI measurements should ideally be performed with pressure and temperature conditions representative of the petroleum reservoirs of interest.

Conventional MR/MRI compatible core holders are typically constructed from rigid polymers or non-porous zirconia[5-9]. These core holders generally utilize commercial RF probes, which are exterior to the core holder[5-9]. Recently, novel MR/MRI compatible core holders have been fabricated from metal alloys with high tensile strength and high thermal conductivityl[10-12]. The metal core holder forms a conductive enclosure, which precludes use of an external RF probe[14]. In these new style MR/MRI compatible metal core holders, the RF probe was placed inside the metallic enclosure[10-12].

In early designs of the metallic core holder, engineering polymers and epoxies were employed to encase the RF probe integrated within the core holder[10-12]. Embedding the RF coil in this manner created a complicated composite structure containing multiple heterogeneous materials. The composite structure, and thereby the RF probe, is vulnerable to damage due to stress cycles associated with the repetitive application and release of pressure in the confining fluid.

This embedded RF probe[10-12] resulted in two other problems: (1) increased $^1$H or $^{19}$F MR background signal due to the $^1$H or $^{19}$F content of the polymeric materials employed, (2) impaired temperature regulation due to the low thermal conductivity of the polymeric materials employed.

A heat exchange jacket enclosed early generation MR/MRI compatible metal core holders with the exterior temperature controlled by a temperature regulated fluid. The polymeric body of the embedded RF probe functioned as thermal insulation between the sample and the regulating fluid.

The embedded RF probe approach also required several complicated high pressure seals to prevent the confining fluid from leaking. This increased the complexity of the fabrication process and complicated assembly/disassembly of the core holder[10-12].

SUMMARY OF THE DISCLOSURE

In one implementation, the present disclosure is directed to an RF probe with an RF coil on a skeletal frame. A sample holder for holding a sample such as a reservoir core plug is housed in the skeletal frame such that the RF coil surrounds the sample. The RF probe and sample holder are adapted to be placed in a core holder (also sometimes referred to as a pressure vessel) with a confining fluid. The sample holder is sealed to isolate the sample from the confining fluid. The RF probe is immersed in the confining fluid when in the core holder.

In another implementation, the present disclosure is directed to a core holder which can hold a confining fluid and includes an RF probe located in the core holder such that when the core holder is filled with the confining fluid, the RF probe is immersed in the confining fluid. The confining fluid also surrounds a sample holder with a sample inside the sample holder, exerting a stress on the sample. The sample can be, for example, a reservoir rock core plug.

In another implementation, the present disclosure is directed to an open frame RF probe adapted for high pressure and high temperature MR/MRI core holder measurements. The open frame is adapted to be submerged in a confining fluid. In certain implementations, the open frame is fabricated from a dielectric insulator, PEEK, preventing conductive losses from the frame. In certain implementations, the RF probe is fabricated using a minimum of polymeric materials and without epoxies.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Probe and Holder Design

Figure 1:
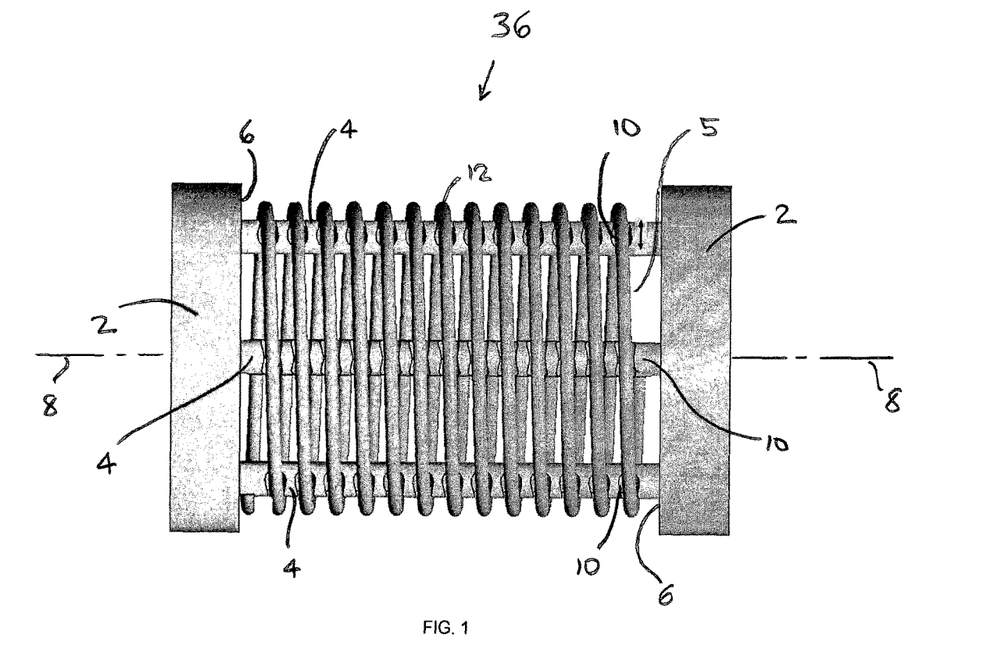
FIG. 1 depicts a side view of an open frame RF probe according to an aspect of the present disclosure.
Figure 2:
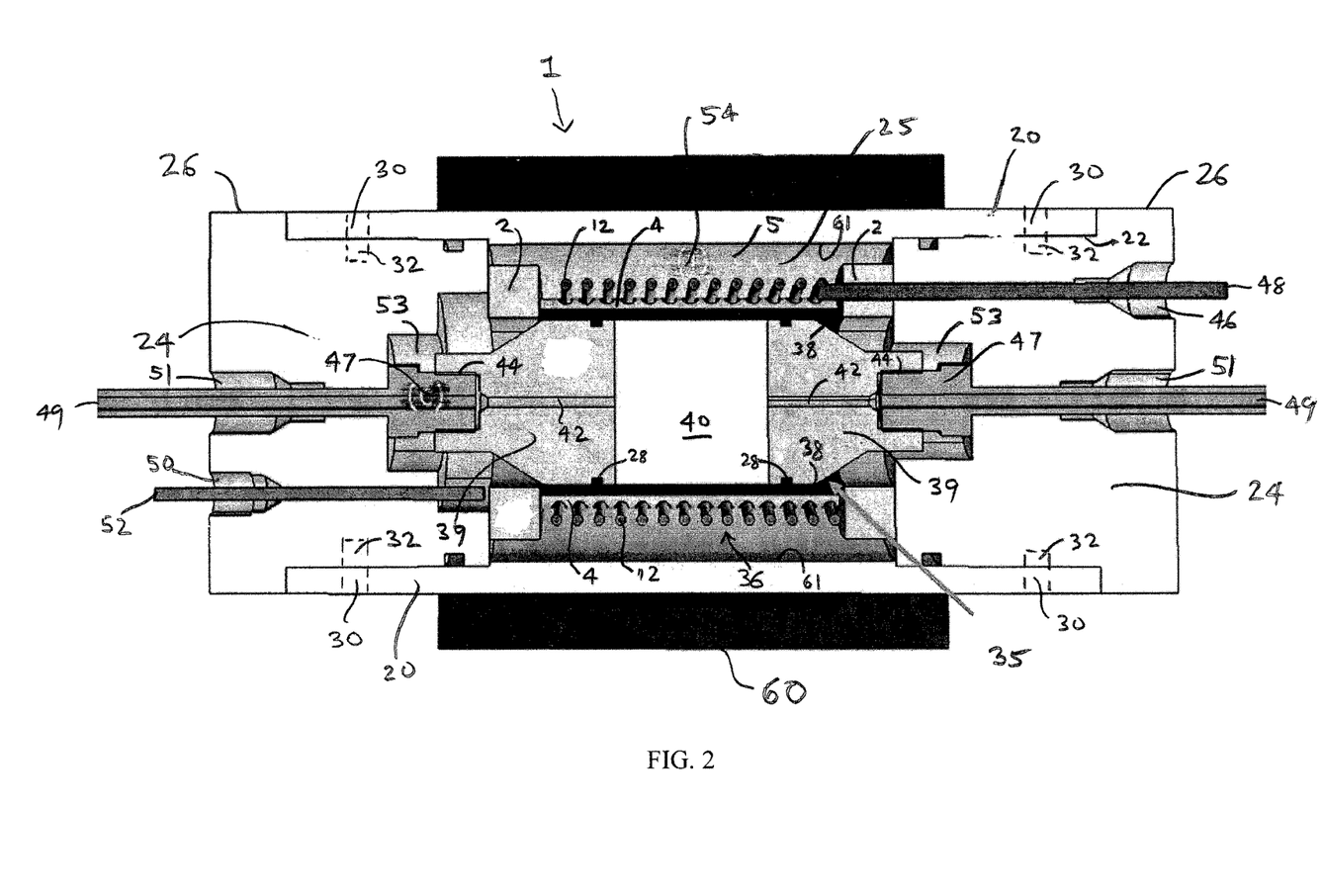
FIG. 2 depicts a side cross-sectional view of a core holder according to an aspect of the present disclosure with the open frame RF probe of FIG. 1 installed therein.

Referring initially to FIG. 1, in one implementation, the present disclosure is directed to an RF probe indicated generally by 36 including a skeletal frame including two spaced end rings 2 interconnected by six (three of the six rods are shown in FIG. 2) rods 4. The end rings 2 include inner faces 6 and the end rings are positioned such that the inner faces 6 are substantially parallel and central axes 8 passing through the end rings 4 are substantially collinear. The rods 4 are spaced around and attached to the inner faces 6 by non-magnetic screws (not shown) but other means of fastening may be used. The longitudinal axes of the rods 4 are substantially parallel. The rods 4 are provided with slots 10 running transverse to the longitudinal axis of the rods for receiving a copper RF coil 12 wound around the rods 4 as a solenoid. Sixteen gauge tinned copper wire (Arcor Electronics, IL, US) is used for the RF coil but other suitable wire may be used. Other coil designs may also be used such as a saddle coil and a birdcage. The slots help position the RF coil windings but can be omitted. The slots 10 have a thread depth of 0.1" but other depths may be used depending for example on the diameter of the wire used for the RF coil 12. A fewer or greater number of rods 4 may be used. The rods 4 enclose a generally cylindrical internal volume 5 having an approximately 1.8" cross-sectional diameter but internal volumes of other dimensions and shapes may be used depending on, for example, the size and shape of the sample being analyzed. The end rings 2 and rods 4 are fabricated from PEEK but other suitable materials may be used such as other polymer composites. In certain embodiments, the materials used should produce a minimal $^1$H and $^{19}$F background signal. The rods 4 are 3" in length and have a ¼" diameter but other lengths and diameters may be used depending for example upon the size and shape of the sample vessel into which the RF probe is designed to be placed.

RF probes according to embodiments of the present invention are adapted to be submerged in confining fluids employed in a sample holder during high pressure MR/MRI measurements. Referring to FIG. 2, a sample holder according to one embodiment of the present invention indicated generally at 1 includes a hollow cylindrical outer casing 20 with open ends 22. Solid cylindrical end closures 24 with flanges 26 close the ends 22. In the present embodiment, both end closures 24 are removable. In other embodiments, one end closure 24 is removable to provide access to the interior of the holder while the other end closure 24 is fixed. The outer casing 20 with the end closures 24 installed define a chamber 25 for housing the RF probe 36. An oil-resistant Buna-N O-ring (McMaster-Carr, OH, USA) 28 on each end closure 24 provides a pressure seal for each end closure 24. The casing 20 and end closures 24 are made of Hastelloy®-C alloy but other suitable metals may be used. Holes 30 are provided in the casing 20 and threaded holes 32 are provided in the end closures 24. When the end closures 24 are inserted in the ends 22 and the holes 32 registered with the threaded holes 32, non-metallic brass screws 34 are inserted into the holes 30 and 32 to secure the end closures 24 in the ends of the 22. Other suitable fasteners can be used in place of the screws 34. A heat exchange jacket 60 surrounds the central section of the casing 20.

Figure 3:
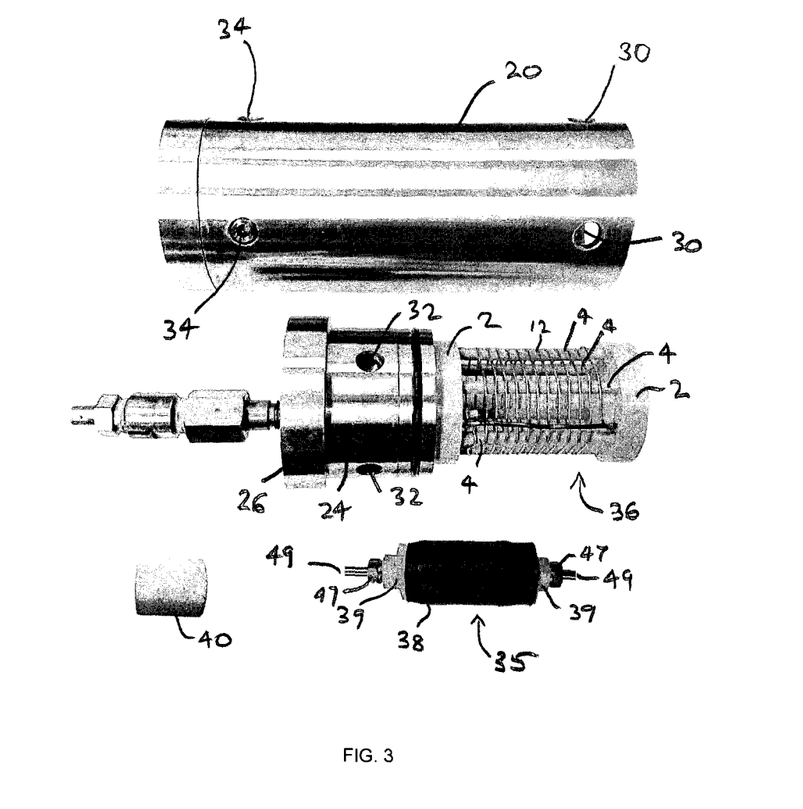
FIG. 3 is photographic images showing side views of components of the core holder of FIG. 2 disassembled according to an aspect of the present disclosure.

Referring also to FIG. 3, the open frame RF probe depicted in FIGS. 1 and 2 is indicated generally at 36 according to an embodiment of the present invention and is attached to end closure 24 which facilitates insertion into and removal from the casing 20 when the end closure 24 is inserted and removed. In other embodiments, the probe 36 is not attached to the end closures 24. A sample holder indicated generally at 35 is adapted to house a sample, such as a 1.5" long Berea sample 40. The sample holder 35 isolates the sample 40 from the confining fluid when the probe 36 is in the sample holder 1. The sample holder 35 includes a containment sleeve 38 of heat shrink tubing which is heat shrunk to sealingly surround the fluid distribution plugs 39 between which is located the sample 40. Each plug 39 includes a fluid conduit 42. Each plug 39 further includes a recess 44 for receiving a tube fitting 47 with a fluid conduit 49 which extend to the outside of the core holder 1 through conduits 51 in the end closures 24. Recesses 53 in the end closures 24 receive the plugs 39 and tube fittings 47.

In operation, sample holder 35 is inserted into the cylindrical internal volume 5 of the RF probe 36 and the RF probe 36 inserted into the chamber 25 of the core holder 1 with the fluid conduits 42 and 49 in fluid communication. The conduits 49 are connectable to a fluid pump (not shown) to circulate fluid to and from the sample 40. Conduit 46 in one of the end closures 24 is provided for solid coax cable 48 (Micro-Coax, PA, US) which is soldered to the RF coil 12 at one end and connectable to an external tuning circuit (not shown) at the other end through a high pressure NPT feedthrough (2846-01-A, CeramTec, SC, US). The NPT feedthrough is connected to a high pressure BNC connector (9263-04-A, CeramTec, SC, US) as shown in FIG. 3. Conduit 50 in the other end closure 24 is provided for a thermocouple 52 to read the temperature of the confining fluid during operation.

When the RF probe 36 with sample holder 35 is in place in the core holder 1, the space within the chamber 25 not occupied by the RF probe 36 and sample holder 35 defines a void space 54 for confining fluid. In the embodiment shown in FIG. 2, the RF coil 12 is spaced from the inner wall 61 of the casing 20. In another embodiment, the RF coil 12 contacts the wall of the casing 20. An inlet (not shown) and an outlet (not shown) in the casing 20 are provided to introduce and remove confining fluid to and from the void space 54.

Frame Material

Without being bound by theory, immersion of the RF probe in the confining fluid may have significant effects on the electrical and mechanical properties of the RF probe, changing the resonance frequency or, for example, decreasing the sensitivity. In certain embodiments of the present invention, PEEK is used for the frame material due to its high bulk modulus, high thermochemical stability, high dielectric strength and low $^1$H and $^{19}$F MR background signal.

PEEK was also an ideal choice due to the simplicity of machining and fabricating PEEK components. Non-porous ceramic materials, such as zirconia, were avoided due to fragility and difficulties in fabrication. Ceramics such as Zirconia also have a higher dielectric constant (relative permittivity), 10-23, compared to PEEK, 2-3, increasing dielectric losses in the probe.

Although the current design is no longer limited by a complicated composite embedded probe[10-12]; one must still consider possible mechanical deformation by isotropic compression (hydrostatic stress)[17]. The bulk modulus of PEEK indicates it will be geometrically stable under isotropic compression up to 700,000 psi[17]. The bulk modulus determines the maximum working pressure when a structure is submerged in high pressure fluids[17]. For conventional core plug measurements, the maximum confining pressure would be 10000 psi[18] insignificant compared to the bulk modulus of PEEK.

PEEK is stable in its mechanical and chemical properties up to a temperature of 250° C. due to its semi-crystalline structure[19]. The dielectric properties of PEEK are constant for frequencies ranging from 100 Hz to 100 MHz in the temperature range from 25 to 200° C.

The open frame RF probe can resist high voltages transmitted during MR/MRI measurements due to the high dielectric strength of PEEK[20]. PEEK is a dielectric insulator with a low loss dielectric and no conductivity loss due to its low relative permittivity and high electrical resistance[20-22]. This decreases the electromagnetic energy dissipation in the open frame RF probe, which substantially increases the Q factor compared to the Q of a RF probe fabricated from non-magnetic materials with high conductivity[20], such as titanium employed by Freeman[15]. The open frame design decreased background MR signal. The PEEK frame also prevents $B_1$ distortions and induced eddy currents in the sample space, improving MR/MRI measurements.

Confining Fluid

When confining fluid is introduced into the void space 54 under pressure, it functions as a thermal and dielectric bath. The confining fluid occupies the void space between the open frame RF probe 3 and the sample holder 35. A pressurizing fluid can change the lump capacitance of an RF probe and consequently its resonance frequency and factor[22,23].

The confining fluid should not contain the nucleus/nuclei that is/are being measured in the sample. In one embodiment, the confining fluid of the present invention, Fluorinert FC-43, Perfluorotri-n-butylamine, (3M Electronic Liquid, MN, U.S.) and silicon oil, Polydimethylsioxane, (Fisher Chemical, ON, CA) were chosen as the confining fluids for measurements at $^1H$ and $^{19}F$ frequencies. Fluorinert FC-43 has no $^1H$ MR signal while silicon oil has no $^{19}F$ MR signal. Fluorinert and silicon oil are dielectric insulators[29] with an electrical resistivity of $10^{14}$-$10^{15}$ Ohm·cm, and a relative permittivity of 1.9-2.7. In other embodiments, for a hydrogen ($^1H$) measurement, other per-fluorinated oils (such as fluorinerts available from 3M) can be used. For a $^{19}F$ measurement, other oils that have no $^{19}F$ may be used. In other embodiments, a perflourinated oil (no H content) can be used. Water ($H_2O$) and heavy water ($D_2O$) were considered as the confining fluid for $^{19}F$ and $^1H$ experiments but each was found to be unsuitable. In other embodiments, nuclei other than $^1H$ and $^{19}F$ can be measured.

The low relative permittivity of Fluorinert and silicon oil slightly increased the lump capacitance of the open frame RF probe. This resulted in a minor change of Q and resonance frequency in the presence of the confining fluid[21]. For $^{19}F$ gas measurements, silicon oil was employed as the confining fluid at a pressure of 1500 psi. Submerging the probe windings in the confining fluid slightly reduced the resonance frequency[22] by approximately 500 KHz at the frequency of 8.04 MHz compared to the probe windings in air.

$H_2O$ or $D_2O$ as the confining fluid significantly increased the lump capacitance, and substantially changed the resonance frequency. The further difficulty of maintaining $D_2O$ proton free when exposed to ambient conditions resulted in silicon oil and fluorinated oil being chosen as the confining fluids.

Imaging

To facilitate studies of $^1H$ and $^{19}F$ gases, one embodiment of the open frame RF probe is designed to be tunable between the $^1H$ and $^{19}F$ frequencies (8.52 MHz and 8.04 MHz) at 0.2 T. The open frame RF probe was employed in $^1H$ $B_1$ mapping and $^{19}F$ gas MR imaging experiments in this work at frequencies of 8.52 MHz and 8.04 MHz respectively. The probe Q was 50 for both frequencies.

One and two dimensional Centric scan SPRITE (Single Point Ramped Imaging with $T_1$ Enhancement) measurements were employed for quantitative imaging of $SF_6$ gas saturating a Berea core plug. Three dimensional centric scan SPRITE measurements were also employed in $^1H$ $B_1$ mapping.

Centric scan SPRITE, employing a short duration RF pulse and a ramped gradient[1,32], is well suited for imaging gas saturation in core plugs at low fields[32]. 1D DHK SPRITE MRI measurement achieves spin density weighted images with short encoding times[32].

$B_1$ Mapping $B_1$ homogeneity can affect quantitative imaging measurements of core plug samples. For example, the SPRITE signal intensity is directly proportional to $B_1^2$, which makes it sensitive to the $B_1$ field distribution in the sample space[31]. A recently developed $B_1$ mapping method[31] was employed to measure the $B_1$ field distribution within the sample space of the open frame RF probe.

Figure 4:
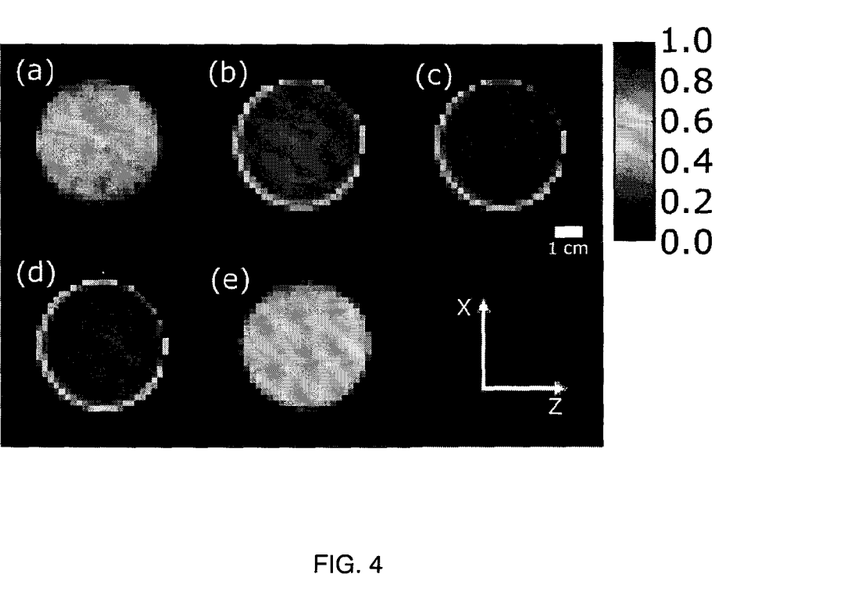
FIG. 4 is images of 2D XZ slices of the normalized $B_1$ field distribution from 3D B1 maps of the RF probe of FIG. 3.

The $^1H$ $B_1$ mapping results are depicted in FIG. 4. Five different planes from the 3D map, (a) to (e), reveal high RF probe homogeneity laterally. (a) and (e) are slices corresponding to the two ends of the RF probe while (b) and (d) are ±0.5 inch displaced from the probe center. The $B_1$ magnetic field is observed to be symmetrically distributed along the long axis of the RF coil. As further shown in FIG. 4 the $B_1$ field intensity diminishes by 13% at displacements of ±0.5 inch axially from the probe center. The open frame RF probe, 3" in length, has an acceptable $B_1$ homogeneity for core plug samples of 1" length and 1.5" diameter.

High Pressure Gas Saturated Core Plug

As a practical test of the open frame RF probe described with reference to FIG. 1, spin density measurements of a core plug saturated with $SF_6$ gas were undertaken with a confining pressure of 1500 psi at a constant temperature of 65° C. Sulfur hexafluoride, $SF_6$, saturated the Berea core plug at pressures of 400 and 500 psi, and a pressure of 600 psi in the supercritical phase, all at a constant temperature of 65° C.[33].

Figure 5:
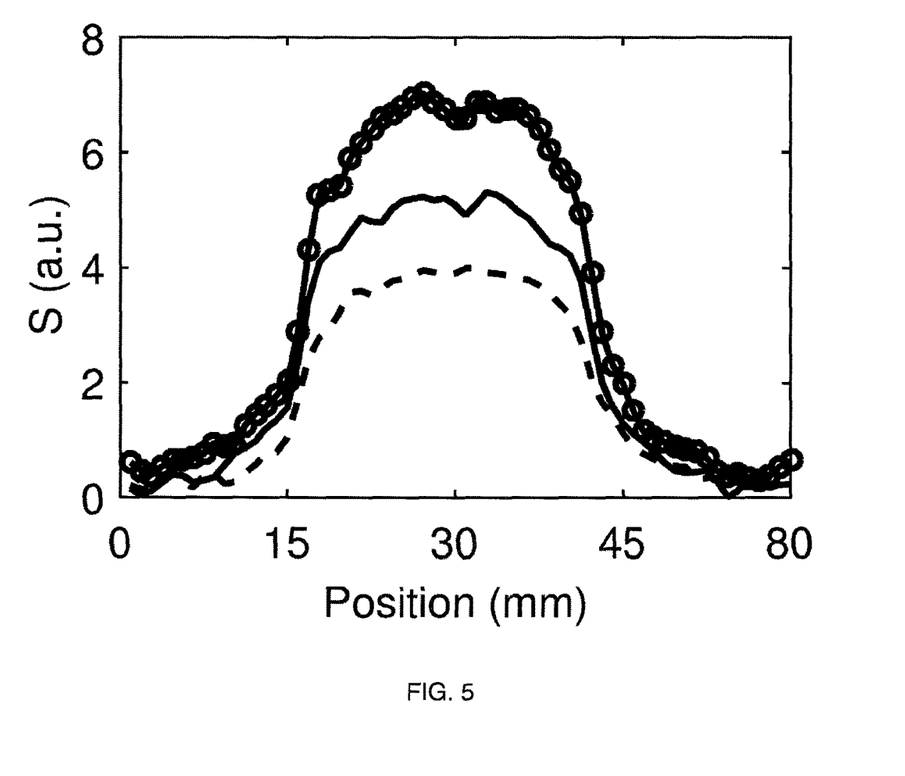
FIG. 5 is a graph of signal intensity from longitudinal 19F profiles of the SF6 saturating the Berea core plug at pressures of 400 psi (---- ¬), 500 psi (-), and 600 psi (θ)
Figure 6:
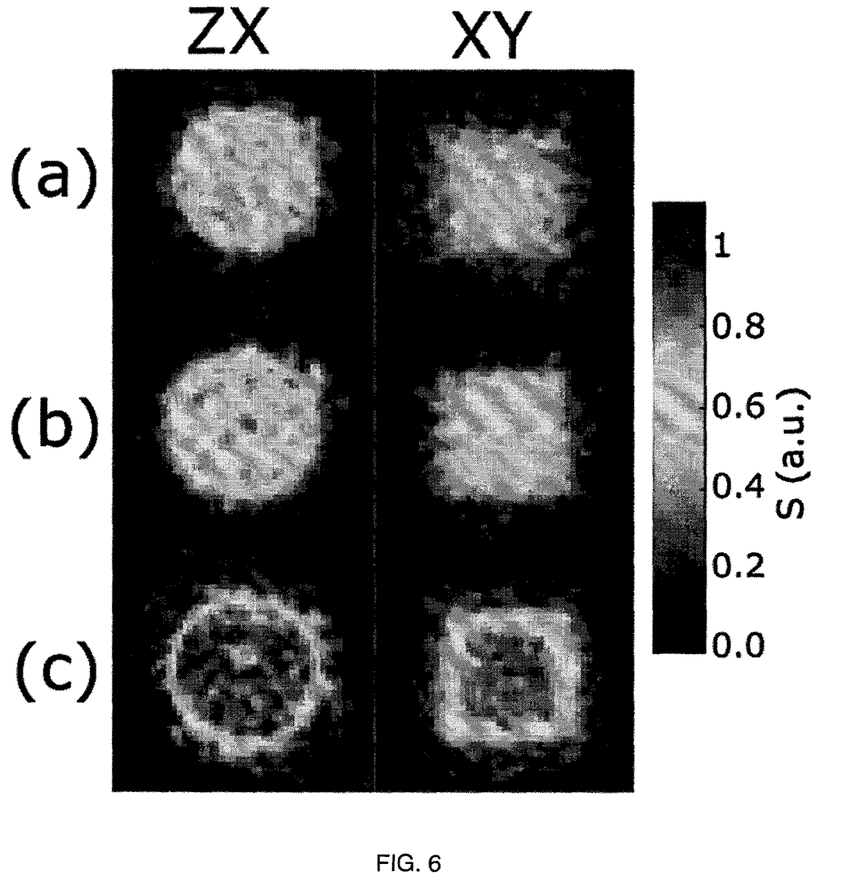
FIG. 6 is 2D centric scan SPRITE images of $SF_6$ in a Berea core plug using the RF probe of FIG. 3.

DHK SPRITE measurements confirmed that the signal intensity varies in direct proportion to the gas pressure, as shown in FIG. 5. Increased pressure increased the signal intensity in direct proportion to the pressure. 2D XY and XZ density maps of $SF_6$ saturated Berea, acquired by 2D centric scan SPRITE, are depicted in FIG. 6. Increasing the gas pressure increased the signal intensity in the fluid density weighted images of FIG. 6. FIG. 6 are 2D centric scan SPRITE images of $SF_6$ in a Berea core plug at pressures of (a) 400 psi, (b) 500 psi, and (c) 600 psi, constant temperature 65° C. The 2D images from (a) to (c) show that increasing the pressure increases the spin density which yields increased signal in centric scan SPRITE images.

The images of FIG. 6 reveal a halo $^{19}F$ signal intensity surrounding the core plug. This signal is thought to originate from $SF_6$ gas penetrating the polymer sleeve that encompasses the core plug with long duration high pressure measurements (two weeks) a background $^{19}F$ signal was observed from the region of the confining fluid. This background signal was due to $SF_6$ gas leakage into the confining fluid.

Temperature and Pressure Control

Temperature can significantly influence MR/MRI core plug measurements[34]. Petrophysical properties of core plugs such as relative permeability and physical properties of fluids saturating core plugs such as viscosity depend on temperature[34,35]. MR/MRI core plug measurements should thus be undertaken at the evaluated temperature of the petroleum reservoir of interest. However, to this point most MR/MRI core plug experiments have been performed at room temperature; due to the difficulties and high cost of high temperature MR/MRI compatible core holders.

The core holder according to an embodiment of the present invention increased in temperature from 25° C. to 65° C., for the $SF_6$ gas experiment described, at a rate of 0.3 C/min. The core holder is fabricated from Hastelloy-C with a 0.3 inch thickness but other suitable materials and thicknesses can be used. The confining fluid surrounding the sample is in direct contact with the interior of the metal core holder. This significantly increases the rate of heat transfer to the sample space.

A non-magnetic Type-T thermocouple and pressure gauges were connected to the closure to monitor the temperature and the confining pressure inside the core holder. The thermocouple head was fully immersed in the confining fluid to ensure accurate temperature readings. The closure shielded the thermocouple head, which prevented the thermocouple from affecting the $B_1$ field distribution. Pressure gauges monitored the gas pressure inside the sample and the core holder during MR/MRI measurements.

EXPERIMENTAL

The open frame RF probe of FIG. 1 was employed for $^1H$ and $^{19}F$ MRI measurements at frequencies of 8.52 MHz and 8.04 MHz in the bore of a Maran DRX-HF, vertical static magnet, operating at 0.2 T (Oxford Instruments Ltd., Oxford, UK). The MRI instrument was equipped with a 1 KW 3445 RF amplifier (TOMCO Technologies, Sydney, Australia) and a three-axis magnetic gradient coil driven by X, Y, Z Techron (Elkhart, Ind.) 7782 gradient amplifiers. The magnetic field gradient coil supplied maximum magnetic gradient fields of 26 G/cm, 24 G/cm and 33 G/cm in the X, Y, Z directions respectively.

In the $B_1$ mapping measurement, a set of 3D centric scan SPRITE images were acquired[33]. The homogenous $^1H$ test sample was a homogeneous amber polyurethane rod (McMaster-Carr, OH, USA), 3" in length with a 1.5" diameter, fully occupying the sample space of the open frame RF probe. The field of view was 60 mm in X and Y directions and 100 mm in the Z direction. The maximum magnetic gradient fields of 17.3 G/cm, 17.3 G/cm and 10.4 G/cm were also employed in directions of X, Y and Z respectively. The phase encoding time was 145 µs with a repetition time, TR, of 2 ms. A delay time of 1.1 s was employed between each of the 39 conical k-space trajectories. The sweep width was 125,000 Hz, k-space points=64×64×64, signal averages=16, and a $P_{90}$=14.3 us with 50% RF power. The RF pulse lengths employed in the 3D SPRITE images were 1.5 µs, 2.5 µs, 3.5 µs, 4.5 µs, 5.5 µs, 6.5 µs and 7.5 µs. The shortest and longest pulse durations corresponded to 1.9° and 9.5° flip angles. Each 3D SPRITE image required approximately 50 min to acquire.

In high pressure MRI measurement, $SF_6$ gas (Praxair, NB, CA) saturated a Berea core plug (Kocurek Industries, TX, USA) of 1.5" length and 1.5" diameter. The Berea sample and the PEEK distributors were enclosed by a piece of silicon rubber tubing (McMaster-Carr, OH, US) and polyolefin plastic tubing (McMaster-Carr, OH, US) employed as the sleeve and heat shrink tubing respectively. Neither the silicon rubber nor polyolefin plastic had a $^{19}F$ MR signal.

The heat exchange jacket illustrated in FIG. 2 regulated the temperature of the confining fluid to 65° C. A Quizix-6000-SS (Vindum Engineering, Ca, US) pump held the confining pressure at 1500 psi.

A Teledyne ISCO 100DX (Teledyne ISCO, Lincoln, Nebr.) pump fed pressurized $SF_6$ gas to the Berea sample and held the pressure constant during high pressure MRI measurements. Prior to pressurizing the core plug sample by $SF_6$, low pressure $SF_6$ was injected into the Berea sample, then purged, to remove air from the pore space.

Each 2D centric scan SPRITE image was acquired with 64×64 k-space points in 2.5 hrs with 512 signal averages acquired. The RF pulse was 15° with duration of 2 µs at 100% RF power. The $t_p$ was 150 µs with a repetition time, TR, of 4 ms. A delay time of 1.5 s (3×$T_1$) was employed between each of the four spiral k-space trajectories. The FOV was 68 mm×68 mm. Maximum magnetic field gradients of 14.7 G/cm and 14.7 G/cm were employed in directions of X and Y, respectively.

The MRI parameters of 1D DHK SPRITE were as above except for the signal averages and the FOV, which were 1024, and 80 mm respectively. A delay time of 2.5 s (5×$T_1$) was employed between the two halves of the single k-space trajectory. A narrow band filter of 125 kHz was employed to prevent $^1H$ and $^{19}F$ MR signal contamination in MRI measurements of the opposite nuclei at 0.2 T static magnetic field[30]. A maximum magnetic field gradient of 12.5 G/cm, was also employed in Y direction.

REFERENCES

[1] C. E. Muir and B. J. Balcom, *Annual reports on NMR Spectroscopy* (Academic Press, Burlington, 2012) edited by G. A. Webb, p. 81.
[2] G. R. Coates, L. Xiao, and Manfred G. Prammer, *NMR Logging Principles & Applications* (Halliburton Energy Services, Houston, 1999), pp. 33-76.
[3] D. Tiab and E. C. Donaldson, *Petrophysics theory and practice of measuring reservior rock and fluid trasnport propertties 2th edition* (Gulf professionmal publishing, Burlington, 2004), pp. 29-86.
[4] *Delivering success in HP/HT reservoirs through experience, innovation and reliable technologies* (Halliburton, Houston, 2011).
[5] Y. Zhao, Y. Song, Y. Liu, H. Liang, and B. Dou, Ind. Eng. Chem. Res. 50, 4707 (2011).
[6] Y. Song, N. Zhu, Y. Zhao, Y. Liu, L. Jiang, and T. Wang, Phys. Fluids. 25, 053301 (2013).
[7] H. Liu, M. Hunter, S. Obruchkov, E. McCarney, M. Robinson, R. Dykstra, and P. Galvosas, *Characterizing fluid presence and transport in rock cores at reservoir-like conditions via spatially resolved NMR relaxation/diffusion maps: The proceedings of the 31st International Symposium of the Society of Core Analysts*, St. John's, Canada, 16-21 Aug. 2015, pp. 143-155.
[8] G. Ersland, J. Husebø, A. Graue, B. A. Baldwin, J. Howard, and J. Stevens, Chem. Eng. J. 158, 25 (2010).
[9] S. A. Bagherzadeh, I. L. Moudrakovski, J. A. Ripmeester, and P. Englezos, Energy. Fuels. 25, 3083 (2011).
[10] H. Han, M. Ouellette, B. MacMillan, F. Goora, R. MacGregor, D. Green, and B. J. Balcom, J. Magn. Reson. 213, 90 (2011).
[11] M. Ouellette, M. LI, G. Liao, E. M. A. Hussein, L. Romero-Zeron, and B. J. Balcom, *Mobile NMR and MRI: Developments and Applications*, edited by M. L. Johns, E. O. Fridjonsson, S. J. Vogt, and A. Haber (Royal Society of Chemistry, Cambridge, 2016), p. 290
[12] A. Afrough, M. Shakerian, S. Zamiri, B. MacMillan, F. Marcia, B. Newling, L. Romero-Zeron, and B. J. Balcom, SPE, Submitted (2017).
[14] R. Morrison, Grounding and shielding: circuits and interference, Wiley-IEEE Press, 2007, pp. 18.
[15] R. Freedman, V. Anand, B. Grant, K. Ganesan, P. Tabrizi, R. Torres, D. Catina, D. Ryan, C. Borman, and C. Krueckl, Rev. Sci. Instrum. 85, 025102 (2014).
[16] D. I. Hoult, Concepts Magn. Reson. 12, 173 (2000).
[17] R. Solechi and R. J. Conant, *Advanced Mechanics of Materials* (Oxford University Press, Inc., New York, 2003), pp. 95-160.
[18] M. A. Andersen, B. Duncan, J. A. Ripmeester, and R. Mclin, Oilfield Review. 25(2),16 (2013).

[19] J. C. Seferis, J. Compos. Mater. 3(4), 158 (1986)

[20] M. Mehdizadeh, *Microwave/RF Applicators and Probes for Material Heating, Sensing, and Plasma Generation A Design Guide* (William Andrew, Oxford, 2010), pp. 2-34.

[21] A. G. Webb, Concepts Magn. Reson. 38A (4), 148 (2000).

[22] J. Mispelter, *NMR Probeheads For Biophysical And Biomedical Experiments: Theoretical Principles And Practical Guidelines* (Imperial College press, London, 2006), pp. 1-91.

[23] W. T. Mclyman, Transformer and inductor design handbook 3th edition, revised and expanded, (Marcel Dekker, Inc, New York, 2004), pp. 456-458.

[24] J. Mitchell, J. Staniland, and R. Chassagne, E. J. Fordham, Transp. Porous. Med. 94, 683 (2012).

[25] C. H. Collie, J. B. Hasted and D. M. Ritson, Proc. Physc. Soc. 60 (2), 145 (1947).

[26] C. H. Wu, C. V. Grant, G. A. Cook, S. H. Park, S. J. Opella, J. Magn. Reson. 200, 74 (2009).

[27] S. W. Atlas, *Magnetic resonance imaging of the brain and spine* 4th edition, (Lippincott williams & wilkins, PA, 2009), pp. 13-18.

[28] D. P. Dewitt, *Fundamentals of Heat and Mass Transfer*, (John Wiley & Sons, Inc., New York, 1996), pp. 581-619.

[29] A. Valori, J. Mitchell, and E. J. Fordham, Concepts. Magn. Reson. 46(B), 202 (2016).

[30] R. K. Minard, A. R. Wind, Concepts. Magn. Reson. 13(2), 128 (2001).

[31] S. Vashaee, B. Newling, B. MacMillan and B. J. Balcom, J. Magn. Reson. 232, 68 (2013).

[32] P. J. Prado, B. J. Balcom, I. V. Mastikhin, A. R. Cross, R. L. Armstrong, and A. Logan, J. Magn. Reson. 137, 324 (1999).

[33] E. W. Lemmon, M. O. McLinden and D. G. Friend, "Thermophysical Properties of Fluid Systems" in *NIST Chemistry WebBook, NIST Standard Reference Database Number 69*, Eds. P. J. Linstrom and W. G. Mallard, National Institute of Standards and Technology, Gaithersburg Md., 20899, doi:10.18434/T4D303.

[34] G. J. Hirasaki, S. W. Lo, Y. Zhang, Y, Magn. Reson. Imaging. 21, 269 (2003).

[35] L. L. Latour, R. L. Kleinberg, A. Sezginer, J. Colloid. Interface. Sci. 150, 535 (1992).

We claim:

1. A core holder for containing a reservoir rock core sample for MR or MRI measurement comprising:
   a casing having sufficient tensile strength to withstand being pressurized to an underground formation pressure, comprising
      a cylindrical wall and end closures for closing the ends of the casing wherein
      at least one of the end closures is removable to provide access to the inside of the casing, the wall and end closures defining a chamber internal to the core holder,
   an inlet and an outlet in the core holder for circulating a confining fluid in the chamber,
   a sample housing in the chamber for containing the core sample, the sample housing comprising
      an inlet and an outlet in the sample holder for circulating fluid to and from the sample, and
   a membrane for isolating the sample from fluid contact with the confining fluid but permitting fluid pressure to be exerted on the sample when the confining fluid is pressurized,
   the space in the chamber not occupied by the sample housing defining a void space,
   a radio frequency probe, connectable to an NMR or MRI apparatus, in the void space and at least partially surrounding the sample housing, whereby confining fluid introduced into the chamber circulates in the void space around the RF probe.

2. The core holder of claim 1, further comprising a frame in the chamber for housing the sample housing and for supporting the RF probe, wherein the void space is further defined by the space in the chamber not occupied by the frame.

3. The core holder of claim 2, wherein the frame is a skeletal frame.

4. The core holder of claim 3, wherein the skeletal frame comprises two end rings held in a spaced and substantially parallel relation by at least two interconnecting rods whereby the central axes of the two end rings are substantially collinear.

5. The core holder of claim 3, wherein the RF probe is wound around the skeletal frame.

6. The core holder of claim 2, wherein the configuration of the RF probe comprises a saddle coil configuration, a bird cage configuration or a solenoid configuration.

7. The core holder of claim 3, wherein the skeletal frame comprises a polymer or a ceramic.

8. The core holder of claim 7, wherein the polymer is PEEK.

9. The core holder of claim 2, further comprising a rock core sample in the sample housing and a confining fluid in the void space, wherein the confining fluid in the void space does not comprise nuclei of the type to be measured in the rock core sample, and wherein the frame and the RF probe are immersed in the confining fluid.

10. The core holder of claim 9, wherein the confining fluid in the void space is a fluorinert or a silicon oil.

11. A method for making an MR or MRI measurement of a reservoir rock core sample in an MR or MRI sample holder, comprising:
   providing a core holder for housing a sample housing for containing the reservoir rock core sample;
   providing a membrane in the core holder for isolating the reservoir rock core sample from fluid contact with a confining fluid but permitting fluid pressure to be exerted on the sample when the confining fluid is pressurized, and wherein space in the core holder not occupied by the sample housing defining a void space;
   providing an exposed radio frequency probe connected to an NMR or MRI apparatus, in the void space and at least partially surrounding the sample housing;
   circulating a fluid in the sample housing; and
   circulating a confining fluid in the void space thereby immersing the exposed radio frequency probe in the confining fluid.

12. The method of claim 11, further comprising externally regulating the temperature of the circulating confining fluid, and thereby regulating the temperature of the sample.

* * * * *